United States Patent [19]

Bhattacharya et al.

[11] Patent Number: 5,352,844

[45] Date of Patent: Oct. 4, 1994

[54] ISOLATION OF PARTIALLY BROMINATED DIPHENYL ETHER MIXTURES IN CRYSTALLINE FORM WITH HIGHER MELTING RANGE

[75] Inventors: Bhabatosh Bhattacharya, Lafayette; Wayne C. Muench, West Lafayette, both of Ind.

[73] Assignee: Great Lakes Chemical Corporation, W. Lafayette, Ind.

[21] Appl. No.: 188,360

[22] Filed: Jan. 27, 1994

Related U.S. Application Data

[63] Continuation of Ser. No. 893,376, Jun. 4, 1992, abandoned.

[51] Int. Cl.$^5$ .................... C07C 41/18; C07C 41/34
[52] U.S. Cl. ........................ 568/639; 568/627
[58] Field of Search ........................ 568/639, 627

[56] References Cited

U.S. PATENT DOCUMENTS

| | | | |
|---|---|---|---|
| 3,833,674 | 9/1974 | Brackenridge | 568/639 |
| 3,959,387 | 5/1976 | Brackenridge | 568/639 |
| 5,000,879 | 3/1991 | Moore, Jr. et al. | 252/604 |
| 5,081,316 | 1/1992 | Hussain | 568/639 |

*Primary Examiner*—Johann Richter
*Assistant Examiner*—Margaret J. Page
*Attorney, Agent, or Firm*—Woodard, Emhardt, Naughton, Moriarty & McNett

[57] ABSTRACT

This invention relates to a process for isolation of partially brominated diphenyl ether mixtures ("Octabrom") having an average bromine content of 7.2–8.5. The process comprises: (i) adding a $C_1$–$C_4$ alkanol to the Octabrom in solution in an organic solvent; (ii) maintaining the contact of the alkanol with Octabrom in the organic solvent for that period of time which is sufficient to allow the Octabrom to precipitate in crystalline form, making a slurry; and (iii) recovering the final Octabrom from the slurry.

28 Claims, No Drawings

ISOLATION OF PARTIALLY BROMINATED DIPHENYL ETHER MIXTURES IN CRYSTALLINE FORM WITH HIGHER MELTING RANGE

This is a continuation of prior application Ser. No. 07/893,376, filed Jun. 4, 1991, now abandoned.

BACKGROUND OF THE INVENTION

Field of the Invention

This invention relates to a process for isolation from solution of partially brominated diphenyl ether mixtures ("Octabrom") having an average of 7.2–8.5 bromine atoms per molecule of diphenyl ether. The isolated Octabrom is crystalline in form, and has a relatively high melting range.

Description of the Prior Art

The flame retardant industry terms and markets mixtures of partially brominated diphenyl ether as "Octabrom". These mixtures, hereafter referred to as Octabrom, are commercially available, typically contain 0–2 weight percent of pentabromodiphenyl ether, 5–15 weight percent of hexabromodiphenyl ether, 40–55 weight percent of heptabromodiphenyl ether, 30–40 weight percent of octabromodiphenyl ether, 5–15 weight percent of nonabromodiphenyl ether, and 0–2 weight percent of decabromodiphenyl ether. The average number of bromine atoms per molecule of brominated diphenyl ether, hereafter referred to as the bromine content, for any particular Octabrom, is dependent on the amounts and the identities of the particular bromo homologs which are present in the Octabrom mixture. The bromine content can be calculated by multiplying the weight percent of each bromo homolog by the number of bromine atoms in that homolog, adding the resulting products and dividing the sum by 100.

Octabrom is a mixture, and therefore does not have a sharp melting point. For purposes herein, the melting point will be expressed as a melting range (M.R.). The melting range can be low, e.g., M.R.=75°–95° C., high, e.g., M.R.=90°–145° C., or can be somewhere in-between, depending on the process and any post-process treatment used in the preparation or production of the Octabrom.

The melting range of any particular Octabrom depends on its amorphous or crystalline nature. The lower melting Octabroms are more amorphous, i.e., much less crystalline, than the higher melting Octabroms which are more crystalline. Another interesting observation is that lower melting Octabroms tend to agglomerate, i.e., tend to form lumps. These lower melting Octabroms can become non free-flowing after being subjected to long storage periods, e.g., a few weeks, and to higher temperatures, e.g., 50°–80° C. during the storage period. Higher melting Octabroms do not have a tendency of agglomeration and are free-flowing.

Apart from the amorphous or crystalline nature of Octabrom and the tendency of agglomeration, Octabrom customers may set melting range as a part of the purchase specifications. Low melt or high melt Octabroms can be required by the Octabrom customers depending on the intended use.

It will be appreciated that there has been a desire to provide Octabroms having a relatively high melting range. Processes have been developed in the prior art for the treatment of slurties of solid Octabrom to increase the melting range. In U.S. Pat. No. 5,000,879, issued to Moore, Jr. et al. on Mar. 19, 1991, there is described a process of forming a slurry of solid Octabrom and a $C_1$–$C_4$ alkanol, maintaining the slurry for a time, generally 1–24 hours, and then separating the treated, solid Octabrom. The Octabrom is washed with water to remove entrained alcohol, and then dried to yield an Octabrom with a higher melting range than the non-treated material. The Moore, Jr. et al. procedure is specifically directed to treating only solid Octabrom, and notes that the low solubility of Octabrom in alkanol is a feature of the process. Similarly, a process for treating solid Octabrom is described in U.S. Pat. No. 5,081,316, issued to Hussain on Jan, 14, 1992, in which the solid Octabrom is slurried in an alkyl halide for a time, and the alkyl halide is then evaporated from the slurry. Hussain requires the use of alkyl halides in which the solid Octabrom is substantially insoluble.

SUMMARY OF THE INVENTION

The present invention provides a method for isolating Octabrom from solution in crystalline form and having a relatively high melting range. In one aspect, the process consists of (i) adding $C_1$–$C_4$ alkanol to the Octabrom in organic solvent(s); (ii) maintaining the contact of alkanol with Octabrom in organic solvent(s) for that period of time which is sufficient to allow the Octabrom to precipitate in crystalline form making a slurry; and (iii) recovering the final Octabrom from the slurry.

It is an object of the present invention to provide an Octabrom product which is crystalline, free-flowing, and non-agglomerating, and which has a relatively high melting range.

A further object of the present invention is to provide a process for producing a high melting range Octabrom product efficiently and at a high rate of recovery.

Another object of the present invention is to provide a process which avoids the need for treating solid Octabrom as a means to obtain a relatively high melting range for the Octabrom.

Further objects and advantages of the present invention will be apparent from the description which follows.

DESCRIPTION OF THE PREFERRED EMBODIMENT

For the purposes of promoting an understanding of the principles of the invention, reference will now be made to the embodiments described hereafter. It will nevertheless be understood that no limitation of the scope of the invention is thereby intended, such alterations, further modifications and applications of the principles of the invention as described herein being contemplated as would normally occur to one skilled in the art to which the invention relates.

The present invention provides a process for the preparation of a solid, crystalline, free-flowing Octabrom product having a relatively high melting range. In the past, Octabrom mixtures have been initially produced in solid form and with relatively lower melting ranges, and the solid product was then treated to increase its melting range. This two-step process can be avoided by the present invention.

Octabrom is a commercially available flame retardant and is well known to the art. In a typical manufacturing process in the prior art, the Octabrom is prepared by bromination of diphenyl ether with liquid bromine in the presence of an iron catalyst. The crude product, consisting of partially brominated diphenyl ethers, is purified by dissovling it in an organic solvent and treating the solution with some kind of neutralizing agent. The Octabrom is then isolated by removing the organic solvent, allowing the residue to solidify, and grinding it to a finely powdered form. This powdered Octabrom is a relatively lower melting product than that obtained by the present invention.

The present process is unique as regards the isolation of the Octabrom. This process gives Octabrom as a crystalline, free-flowing, non-agglomerating, and higher melting solid directly from the solution in organic solvent. This avoids isolating the Octabrom in lower melting form and then raising its melting range by some other treatment. Moreover, it reduces or avoids the significant time required in the prior art for removal of organic solvent, solidification of the lower melting Octabrom to its amorphous form (perhaps a few days in production scale), debricking the glassy cake, and grinding the Octabrom to powder form. The time, expense and inconvenience of post-recovery treatments to raise the melting range are also avoided. The isolation procedure avoids the lower melting Octabrom which can have agglomerating problems, and provides a higher melting product for which the agglomerating problem is minimized or non-existent.

At this point it should be understood that a higher melting range for the Octabrom is intended to mean that the isolated product obtained by the present invention has a melting range in which the lowest temperature, the highest temperature or both temperatures are higher than the corresponding temperature(s) which define the melting range of the Octabrom if it were isolated simply by removing the organic solvent in which the Octabrom was dissolved and allowing it to solidify to give the amorphous Octabrom. It is also to be understood that there is a practical limit to the higher melting range which can be achieved by the process of the invention. For example, it may not be practical to have a product with the lowest temperature of 130° C. and the highest temperature of 160° C.

The present process is of value in isolating Octabrom products to have a higher melting range than would have occurred under the prior art process for initially preparing the Octabrom. For example, by the prior art process a produced Octabrom mixture may have had a lower melting range in which the lowest temperature in the range was from about 65° C. to about 86° C., and in which the highest temperature in the range was from about 95° C. to about 120° C. By using the present process, the resulting Octabrom product, as initially recovered, will have a significantly increased melting range and will be more crystalline and free-flowing. Further, the prior art process may have yielded an Octabrom product having a relatively higher melting range, e.g., one in which the lowest temperature in the melting range was from about 79° C. to about 105° C. and in which the highest temperature in the melting range was from about 120° C. to about 135° C. While the latter Octabrom might not have an agglomerating problem, it still may be desirable to isolate such an Octabrom by means of the present invention to yield a still higher melting range. Even an Octabrom having a very high melting range, e.g., 100-140° C., can have its melting range improved by the isolation procedure of the present invention.

In accordance with the present invention, a solution of Octabrom in an organic solvent is utilized. This solution is conveniently obtained as the mixture produced upon dissolution of the crude product obtained by the initial bromination of the diphenyl ether with liquid bromine. The bromination of diphenyl ether and subsequent dissolution of the crude product in organic solvent as a preliminary to isolating the Octabrom, and the organic solvents useful therefor, are well known in the prior art. These organic solvents may include, for example, benzene, toluene, xylenes and the like, with toluene being most preferred.

In accordance with the present invention, the produced Octabrom is not isolated from this solution. Rather, a $C_1$-$C_4$ alkanol is first added to the solution. A higher melting range Octabrom is then directly recovered from the solution, e.g., by crystallization. Alternatively, recovered Octabrom, including commercially available Octabrom, may be dissolved in organic solvent and the $C_1$-$C_4$ alkanol combined with this solution, and a higher melting Octabrom is obtained therefrom.

The alkanol used in isolating the Octabrom from solution is a $C_1$-$C_4$ alkanol. The term $C_1$-$C_4$ alkanol includes individual alcohols containing 1-4 carbon atoms and any mixtures of two or more of such alcohols. Individual alcohols include methanol, ethanol, propanol, isopropanol, butanol, isobutanol, and t-butanol. Methanol, ethanol and mixtures thereof are preferred, with methanol being most preferred.

Octabrom is not very soluble in $C_1$-$C_4$ alkanols. In fact, solubility of Octabrom is 0.5 g/100 g of alkanol at 23° C. Similarly, Octabrom is very slightly soluble in organic solvents, such as benzene, toluene, xylenes, etc. at ambient temperature. As a result, there is little difference in the bromo homolog distribution between the lower melting starting Octabrom obtained by simply removing the solvent and the higher melting final Octabrom obtained by the process of isolation of the present invention. Thus, the product specifications are not adversely affected.

Isolation of the Octabrom may be carried out by adding alkanol to the Octabrom solution in organic solvent or vice versa, in the presence or absence of "seed". The term "seed" refers to the relatively higher melting Octabrom which will ultimately be obtained by the isolation procedure. The isolation can conveniently be carried out at ambient temperature, there being no observed advantage from using higher than ambient temperatures. Temperatures within the range of about 25°-85° C. are suitable. The pressure during the isolation procedure is conveniently atmospheric.

The amount of alkanol used is not critical and is simply that amount which produces crystalline product at a desirable yield. For example, a preferred amount of alkanol would be about 110 g to about 120 g of alkanol per 40 g of toluene. However, the amount of alkanol for a given system can vary widely, and preferred amounts can be readily determined by one skilled in tile art by routine. Generally, contact periods of alkanol with the Octabrom in organic solvent for about 1 hour to about 8 hours are sufficient for most situations. A preferred contact period is about 2 hours to about 6 hours.

In practice, a preparation is provided which includes the Octabrom in an organic solvent at a temperature sufficiently high that the Octabrom is dissolved in the solvent. The Octabrom will precipitate out of this solution, particularly with cooling. Temperatures may range from 25° C. to 85° C., and in particular the recovery of the final Octabrom product may occur within this range or with cooling of the preparation from a higher temperature, for example to 25° C. Seed may be added to the preparation before or after the combination therewith of the alkanol, or may already be present in the preparation as an initial precipitate prior to addition of the alkanol.

The invention will be further described with reference to the following specific Examples. However, it will be understood that these Examples are illustrative and not restrictive in nature.

EXAMPLES 1-6

For each example, 40 g of Octabrom (GLCC DE-79®) and 16 g of toluene were charged into a 250 ml 3-neck flask fitted with a mechanical stirrer, thermometer, and reflux condenser. DE-79® is an Octabrom product available commercially from Great Lakes Chemical Corporation and having a melting range of 80°–90° C. The mixture was heated under stirring until a clear solution was obtained (~80° C.). Time solution was cooled to the specified contact temperature, and 47.5 g of methanol was added to it, in the presence or absence of "seed", under vigorous stirring at such a rate that the Octabrom separated in crystalline form. The contact time was 3.5 hours in all cases. After the contact period, the suspension was cooled to 25° C. and filtered. The wet cake was washed once with 8 ml of methanol and dried in air to constant weight.

EXAMPLE 7

This procedure was similar to that of Example 1, except that the solvents were removed from the product by stripping the slurry at 30° C. under reduced pressure, instead of removing by filtration.

EXAMPLE 8

This procedure was similar to that of Example 1, except that the mode of addition was reversed, i.e., the toluene solution of DE-79® was added to the methanol at 25° C.

EXAMPLES 9-10

The procedure of Example 1 was repeated, except that ethanol and rn-butanol, respectively, was added into the solution of DE-79® in toluene at 25° C.

EXAMPLES 11-12

The procedure of Example 1 was repeated, except that methanol was added into a solution of DE-79® in benzene and xylenes, respectively.

EXAMPLES 13-15

Forty grams of Octabrom (GLCC DE-79H®) was dissolved in 16 g of toluene in a 250 ml flask at ~80° C. and cooled to 25° C. DE-79H is an Octabrom product available from Great Lakes Chemical Corporation and having a melting range of 79°–105° C. To the mixture was added 47.5 g of methanol at such a rate that the Octabrom separated in crystalline form (3.5 hours). The solid was filtered off, washed with 8 ml of methanol, and dried in air. Similar treatments of toluene solutions of DE-79H® with ethanol and n-butanol separately gave crystalline Octabroms.

The melting ranges of the starting DE-79®, DE-79H® and the final Octabroms isolated by the process of the present invention were determined with a Büchi Melting Point Apparatus, Model #510, and are presented below in TABLE I.

TABLE I

| Example # | Alkanol | Organic Solvent | "Seed" on DE-79® | Contact Temp.°C. | M.P.°C. |
|---|---|---|---|---|---|
| Starting DE-79® | — | — | — | — | 80–90 |
| 1 | MeOH | Toluene | — | 25 | 122–135 |
| 2 | MeOH | Toluene | — | 59–60 | 120–130 |
| 3 | MeOH | Toluene | 0.25% | 25 | 115–135 |
| 4 | MeOH | Toluene | 0.25% | 23–52 | 121–134 |
| 5 | MeOH | Toluene | 0.25% | 15–16 | 123–137 |
| 6 | MeOH | Toluene | 0.125% | 25 | 124–135 |
| 7* | MeOH | Toluene | — | 25 | 124–132 |
| 8** | MeOH | Toluene | — | 25 | 114–131 |
| 9 | EtOH | Toluene | — | 25 | 122–135 |
| 10 | n-BuOH | Toluene | — | 25 | 122–135 |
| 11 | MeOH | Benzene | — | 25 | 122–134 |
| 12 | MeOH | Xylenes | — | 25 | 119–134 |
| Starting DE-79H® | — | — | — | — | 79–105 |
| 13 | MeOH | Toluene | — | 25 | 128–150 |
| 14 | EtOH | Toluene | — | 25 | 128–150 |
| 15 | n-BuOH | Toluene | — | 25 | 128–150 |

*Solid was isolated by evaporating the slurry to dryness at 30° C./vacuum.
**Toluene solution of DE-79® added to MeOH.

The isomer distribution of the starting DE-79®, DE-79H® and exemplary ones of the final Octabroms isolated by the process of the present invention were determined and are given in TABLE II.

TABLE II

| Example # | Area % | | | | | |
|---|---|---|---|---|---|---|
| | $Br_5$ | $Br_6$ | $Br_7$ | $Br_8$ | $Br_9$ | $Br_{10}$ |
| Starting DE-79® | 0.6 | 10.6 | 44.4 | 31.2 | 11.1 | 0.9 |
| 1 | 0.5 | 10.0 | 43.1 | 30.8 | 13.4 | 1.8 |
| 9 | 0.5 | 9.8 | 44.7 | 32.5 | 11.3 | 0.8 |
| 10 | 0.4 | 9.5 | 44.6 | 32.8 | 11.4 | 0.8 |
| 11 | 0.6 | 10.4 | 44.3 | 31.8 | 11.4 | 0.9 |
| 12 | 0.5 | 10.3 | 44.6 | 32.0 | 11.3 | 0.9 |
| Starting DE-79H® | 0.5 | 4.7 | 38.8 | 36.6 | 17.0 | 1.7 |
| 13 | 0.3 | 4.1 | 37.8 | 37.6 | 18.0 | 1.8 |
| 14 | 0.3 | 3.6 | 38.2 | 37.8 | 18.0 | 1.8 |
| 15 | 0.2 | 3.0 | 37.6 | 38.4 | 18.5 | 2.0 |

EXAMPLE 16

Repetition of the foregoing procedures using various combinations of diphenyl ether mixtures, organic solvents, and $C_1$–$C_4$ alkanols yields similar results. The partially brominated diphenyl ethers include various amounts of pentabromodiphenyl ether, hexabromodiphenyl ether, heptabromodiphenyl ether, octabromodiphenyl ether, nonabromodiphenyl ether and decabromodiphenyl ether, and mixtures thereof. The organic solvents include benzene, toluene, xylenes and mixtures thereof. The $C_1$–$C_4$ alkanols include methanol, ethanol, propanol, isopropanol, butanol, isobutanol and t-butanol, and mixtures thereof. Repetition of the previous examples using different combinations of the three foregoing components yields diphenyl ether products having a relatively higher melting range than for the corresponding preparation processes without the use of the alkanols prior to isolation of the diphenyl ethers.

While the invention has been described in detail in the foregoing description and its specific Examples, the same is to be considered as illustrative and not restrictive in character. It is to be understood that only the preferred embodiments have been described, and that all changes and modifications that come within the spirit of the invention are desired to be protected.

What is claimed is:

1. A method for the isolation of a solid partially brominated diphenyl ether product from a mixture of partially bromnated diphenyl ethers having an average of from about 7.2 to ab out 8.5 bromine atoms per molecule of diphenyl ether, the method comprising:
   a. providing a mixture of partially brominated diphenyl ethers, wherein said mixture has been removed form its bromination medium;
   b. dissolving the mixture in an organic solvent selected from the group consisting of benzene, toluene, and xylenes, or mixtures thereof, at a temperature sufficiently high for the partially brominated diphenyl ethers and solvent to form a solution,
   c. contacting the solution of step b with a $C_1$–$C_4$ alkanol;
   d. maintaining the contact of step c, for a sufficient time to allow said diphenyl ether product to precipitate out; and
   e. recovering the precipitate.

2. The method of claim 1 in which step d, also comprises cooling the mixture of step c.

3. The method of claim 1 in which the mixture of partially brominated diphenyl ethers contains ethers selected from the group consisting of pentabromodiphenyl ether, hexabromodiphenyl ether, heptabromodiphenyl ether, octabromodiphenyl ether, nonabromodiphenyl ether or decabromodiphenyl ether, and mixtures thereof.

4. The method of claim 1 in which the $C_1$–$C_4$ alkanol is selected from the group consisting of methanol, ethanol, propanol, isopropanol, butanol, isobutanol and t-butanol, or mixtures thereof.

5. The method of claim 4 in which the alkanol is selected from the group consisting of methanol, ethanol, or mixtures thereof.

6. The method of claim 5 in which the alkanol is methanol.

7. The method of claim 1 and which includes maintaining the contact for between about 1 to about 8 hours prior to the recovering step e.

8. The method of claim 7 in which said maintaining is between about 2 hours and about 6 hours.

9. The method of claim 7 in which said maintaining is at a temperature of between about 25° C. and about 85° C.

10. The method of claim 9 in which said maintaining is at a temperature of about 25° C.

11. A method for the isolation of a solid partially brominated diphenyl ether product from a mixture of partially brominated diphenyl ethers having an average of from about 7.2 to about 8.5 bromine atoms per molecule of diphenyl ether, the method comprising:
    a. providing a solution of the partially brominated diphenyl ethers in an organic solvent at a temperature sufficiently high for the partially brominated diphenyl esters to be dissolve din the organic solvent;
    b. contacting the solution of step a, with a $C_1$–$C_4$ alkanol;
    c. maintaining the contact of step b, for a sufficient time to allow said diphenyl ether product to precipitate out; and
    d. recovering the precipitate;
wherein the organic solvent is selected from the group consisting of benzene, toluene, and xylenes, or mixtures thereof.

12. The method of claim 11 in which the organic solvent is toluene.

13. A method for isolating a solid dipheny ether product having an average of from about 7.2 to about 8.5 bromine atoms per molecule of diphenyl ether from a mixture of partially brominated diphenyl ethers, wherein said mixture has been removed from its bromination medium, the method including contacting said mixture of partially brominated diphenyl ethers with a $C_1$–$C_4$ alkanol to form a product mixture and recovering said product from said product mixture, wherein the improvement comprises:
    prior to said contacting of a $C_1$–$C_4$ alkanol, providing a solution of said mixture of partially brominated diphenyl ethers in an organic solvent selected from the group consisting of benzene, toluene, and xylenes, or mixtures thereof, at a temperature sufficiently high for said mixture of partially brominated diphenyl ethers to be dissolved in said organic solvent.

14. The improvement of claim 13 in which the recovering comprises precipitating out the diphenyl ether product from said product mixture.

15. The improvement of claim 13 in which the mixture of partially brominated diphenyl ethers contains ethers selected from the group consisting of pentabromodiphenyl ether, hexabromodiphenyl ether, heptabromodiphenyl ether, octabromodiphenyl ether, nonabromodiphenyl ether and decabromodiphenyl ether, or mixtures thereof.

16. The improvement of claim 13 in which the $C_1$–$C_4$ alkanol is selected from tile group consisting of methanol, ethanol, propanol, isopropanol, butanol, isobutanol and t-butanol, or mixtures thereof.

17. The improvement of claim 16 in which the alkanol is selected from the group cons]sting of methanol, ethanol, or mixtures thereof.

18. The improvement of claim 17 in which the alkanol is methanol.

19. The improvement of claim 13 which includes maintaining said product mixture for between about 1 hour to abut 8 hours prior to the recovering of said product.

20. The improvement of claim 19 in which said maintaining is for between about 2 hours and about 6 hours.

21. The improvement of claim 19 in which said maintaining is at a temperature of between about 25° C. and about 85° C.

22. The improvement of claim 19 in which said maintaining is at a temperature of about 25° C.

23. The improvement of claim 13 in which said recovering includes adding seed to said product mixture.

24. A method for isolating a solid diphenyl ether product having an average of from about 7.2 to about 8.5 bromine atoms per molecule of diphenyl ether from a mixture of partially brominated diphenyl ethers, the method including contacting said mixture of partially brominated diphenyl ethers with a $C_1$–$C_4$ alkanol to form a product mixture and recovering said product from said product mixture, wherein the improvement comprises:
    prior to said contacting of a $C_1$–$C_4$ alkanol, providing a solution of said mixture of partially brominated diphenyl ethers in an organic solvent at a temperature sufficiently high for said mixture of partially brominated diphenyl ethers to be dissolved in said organic solvent, wherein the organic solvent is selected from the group consisting of benzene, toluene, and xylenes, or mixtures thereof.

25. The improvement of claim 24 in which the organic solvent is toluene.

26. A method for the isolation of a solid partially brominated diphenyl ether product from a mixture of partially brominated diphenyl ethers having an average of from about 7.2 to about 8.5 bromine atom per molecule of diphenyl ether, the method comprising:
   a. brominating diphenyl ether in liquid bromine in the presence of a bromination catalyst to afford a mixture of partially brominated diphenyl ethers;
   b. dissolving said mixture in an organic solvent selected from the group consisting of benzene, toluene, and xylenes, or mixtures thereof, at a temperature sufficiently high for the partially brominated diphenyl ethers to be dissolved in the organic solvent;
   c. contacting the solution of step (b) with a $C_1$–$C_4$ alkanol;
   d. maintaining the contact of step (c) for a sufficient time to allow said diphenyl ether product to precipitate out; and
   e. recovering the precipitate.

27. The method of claim 26 in which step d also comprises cooling the mixture of step c.

28. The method of claim 26 in which the $C_1$–$C_4$ alkanol is selected from the group consisting of methanol, ethanol, propanol, isopropanol, butanol, isobutanol and t-butanol, or mixtures thereof.

* * * * *